(12) United States Patent
Kennedy McConnell et al.

(10) Patent No.: US 10,512,416 B2
(45) Date of Patent: Dec. 24, 2019

(54) ESTIMATION OF BLOOD FLOW RATES

(71) Applicant: Isis Innovation Ltd., Oxford (GB)

(72) Inventors: Flora A. Kennedy McConnell, Oxford (GB); Stephen J. Payne, Oxford (GB); Michael A. Chappell, Oxford (GB); Thomas W. Okell, Oxford (GB)

(73) Assignee: Oxford University Innovation Limited (GB)

(*) Notice: Subject to any disclaimer, the term of this patent is extended or adjusted under 35 U.S.C. 154(b) by 987 days.

(21) Appl. No.: 14/938,250

(22) Filed: Nov. 11, 2015

(65) Prior Publication Data

US 2016/0128601 A1    May 12, 2016

Related U.S. Application Data

(60) Provisional application No. 62/078,550, filed on Nov. 12, 2014.

(51) Int. Cl.
*A61B 5/055* (2006.01)
*A61B 5/026* (2006.01)
*G01R 33/563* (2006.01)

(52) U.S. Cl.
CPC ............ *A61B 5/055* (2013.01); *A61B 5/0263* (2013.01); *G01R 33/56308* (2013.01); *G01R 33/5635* (2013.01); *G01R 33/56366* (2013.01)

(58) Field of Classification Search
USPC ....................................................... 600/431
See application file for complete search history.

(56) References Cited

U.S. PATENT DOCUMENTS

| | | | | |
|---|---|---|---|---|
| 2007/0016074 | A1* | 1/2007 | Abreu | A61B 3/1241 600/475 |
| 2015/0223724 | A1* | 8/2015 | Hauck | A61B 5/0538 600/373 |
| 2016/0113576 | A1* | 4/2016 | Hulvershorn | A61B 5/0215 600/301 |
| 2016/0374612 | A9* | 12/2016 | Hulvershorn | A61B 5/0215 600/301 |

* cited by examiner

*Primary Examiner* — Pierre E Elisca
(74) *Attorney, Agent, or Firm* — Thomas|Horstemeyer, LLP (57) ABSTRACT

Disclosed are various embodiments for estimating the flow of blood through a blood vessel in a region of interest. Passage of a bolus of fluid through an imaged blood vessel over a period of time is tracked by a computing device. The computing device fits the tracked passage of the bolus of fluid to a modeled passage of the bolus of fluid. The computing device then estimates a volume of blood flow through the imaged blood vessel based at least in part on a fit of the tracked passage of the bolus of fluid to the modeled passage of the bolus of fluid.

20 Claims, 5 Drawing Sheets

ESTIMATION OF BLOOD FLOW RATES

CROSS-REFERENCE TO RELATED APPLICATIONS

This application claims priority to and the benefit of U.S. Provisional Application No. 62/078,550, entitled "Estimation of Blood Flow Rates" and filed on Nov. 12, 2014, which is incorporated by reference as if set forth herein in its entirety.

TECHNICAL FIELD

The present disclosure generally relates to medical imaging and more particularly, relates to systems and methods for providing clinicians with quantitative blood volume flow rate information to help make diagnostic, prognostic, or therapeutic decisions.

BACKGROUND

Angiographic methods, which generate images of blood vessels, are of great importance in the assessment of vascular diseases, such as atherosclerosis. They can provide information on vessel morphology and function which aids clinicians with diagnosis, prognosis, and treatment planning in these patients. Vessel-selective angiography provides additional information about the relative importance of each feeding artery which can be useful in a number of areas, such as the assessment of collateral blood flow or the evaluation of blood supply to a tumor or arteriovenous malformation. However, many angiographic methods provide only qualitative information on blood flow, making objective comparisons between vessels and across subjects difficult. In addition, many of these methods have a number of other drawbacks such as the requirement for an invasive procedure, the use of ionizing radiation, or the administration of a contrast agent.

SUMMARY

Described herein are various angiographic systems and methods for quantifying blood flow rates in a vessel segment, such as an arterial segment. The flow rates can be quantified from dynamic angiographic data. The methods do not require an invasive procedure, ionizing radiation, or the administration of a contrast agent.

In various embodiments, the systems and methods can provide estimation of haemodynamic parameters by fitting a fluid mechanics derived model to the data. In various aspects, a total ASL signal time series as measured in a vessel segment, such as an arterial segment, (the sum of the time series from each voxel in the segment) considering the mass transport of ASL labelled blood is applied for estimation of blood flow through the vessel. The methods can include the effects of $T_1$ decay, RF attenuation, and contrast bolus dispersion due to non-axial velocity profile of blood flow. The methods provide the ability to obtain information about flow conditions in, for example, the cerebral vasculature. Observing a trend towards a difference, in such conditions, between healthy and diseased vascular networks can provide an understanding of cerebrovascular disease, and can provide diagnostic markers of such diseases.

In an embodiment, a system for estimating blood flow rates through a vessel is provided considering the mass transport of blood through a region of interest of the vessel. The system can comprise: at least one computing device; an imaging device in data communication with the at least one computing device; and an application executed in the at least one computing device, the application comprising machine readable instructions that, when executed, cause the at least one computing device to at least: identify a passage of a bolus of fluid through a region of interest of an imaged blood vessel over a period of time; and estimate, with a mass transit model, blood flow through the region of interest of the imaged blood vessel based at least in part on the passage of the bolus of fluid through region of interest of the imaged blood vessel during the period of time.

In any one or more aspects of the system, causing the at least one computing device to estimate the blood flow through the imaged blood vessel can further comprise causing the at least one computing device to at least estimate the blood flow based at least in part on an anatomical data of the blood vessel. The bolus of fluid can comprise an arterial spin labeling (ASL) tagged bolus of fluid. The ASL tagged bolus of fluid can correspond to a pulsed ASL tagged bolus of fluid. The ASL tagged bolus of fluid can corresponds to a pseudo-continuous ASL tagged bolus of fluid. The arterial spin labeling (ASL) tagged bolus of fluid can have a box-car signal profile. The mass transit model can include an axial velocity profile of the bolus of fluid. Causing the at least one computing device to at least estimate, with a mass transit model, blood flow through the region of interest of the imaged blood vessel can estimate variation in axial velocity with radius of the bolus of fluid passing through the region of interest of the imaged blood vessel. The application can cause the at least one computing device to at least acquire dynamic angiographic data which covers the region of interest of the imaged blood vessel in a subject. Causing the at least one computing device to acquire the dynamic angiographic data can comprise causing the at least one computing device to acquire the angiographic data from a medical imaging device, and wherein the subject is positioned in association with the medical imaging device and the medical imaging device is used to acquire the dynamic angiographic data.

In an embodiment, a method for estimating blood flow through a vessel is provided considering the mass transport of blood through a region of interest of the vessel. The method can comprise: tracking, via a computing device, a passage of a bolus of fluid through an imaged blood vessel over a period of time; fitting, via the computing device, the tracked passage of the bolus of fluid to a modeled passage of the bolus of fluid, wherein the modeled passage of the bolus of fluid is based at least in part on a mass transit model; and estimating, via the computing device, a volume of blood flow through the imaged blood vessel based at least in part on a fit of the tracked passage of the bolus of fluid to the modeled passage of the bolus of fluid.

In any one or more aspects, the method can comprise initializing, via the computing device, the modeled passage of the bolus of fluid based at least in part on anatomical data of the imaged blood vessel. The fitting of the tracked passage of the bolus of fluid to the modeled passage of the bolus of fluid can be based at least in part upon a direct search method. The direct search method can comprise a Nelder-Mead simplex approach. The bolus of fluid can comprise a pulsed arterial spin labeling (ASL) tagged bolus of fluid. The bolus of fluid can comprise a pseudo-continuous arterial spin labeling (ASL) tagged bolus of fluid. The mass transit model can include an axial velocity profile of the bolus of fluid. The mass transit model can estimate variation in axial velocity with radius of the bolus of fluid passing through the region of interest of the imaged blood vessel. The method can comprise acquiring dynamic angiographic data which covers the region of interest of the imaged blood vessel in a subject. The acquiring of the dynamic angiographic data can comprise acquiring the angiographic data from a medical imaging device, positioning the subject in association with the medical imaging device, and using the medical imaging device to acquire the dynamic angiographic data.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Disclosed are various embodiments for performing quantitative arterial spin labeling (ASL) magnetic resonance angiography (MRA). The ASL MR signal measured in a region of interest (ROI) of a vessel can be modelled by considering the mass transport of an ASL tagged bolus of fluid, and integrating the signal it produces over the volume of the region, according to the various embodiments of the present disclosure. In various aspects, pulsed ASL approaches or pseudo-continuous ASL approaches can be used to tag the bolus of fluid. In various aspects the fluid can be blood, and the vessel segments can be arterial segments. This allows for estimation of blood flow parameters in vessel segments that are much shorter than the arterial segments used in other angiographic methods. A more detailed quantification of blood flow and haemodynamics along an entire arterial vascular tree in the brain of a subject, such as an individual patient, can be provided.

In various aspects, estimation of blood flow parameters can be performed by modeling an ASL tracer signal in an ROI of an angiogram. A plurality of individual voxel signals can be obtained, and the total signal can be the sum of each of the individual voxel signals. The present region based approach requires much less computation time than existing methods which fit a model to each voxel in turn. The present systems and methods can be easier to implement for use by clinicians/radiographers on MR apparatus in a clinical context than prior approaches.

In one or more aspects the modeling of the ASL tracer signal can assume the creation of a tracer bolus with a box-car signal profile. The progression of the bolus through a vessel to an ROI can be estimated. The total modeled signal in the ROI can take into account signal attenuation effects and dispersion of the bolus.

In various aspects, the present disclosure provides a new application of the mass transport of a detectable fluid, for example blood, through an ROI, and modeling dispersion in terms of fluid flow profile, to the analysis of ASL MR angiography. The ROI may include a vessel, such as a blood vessel. By using fluid mechanics to model the total summed signal in an ROI the present method can be used to estimate blood flow in small vessel segments. This removes the necessity of including all of the ASL tagged blood bolus in the region of the image considered. Thus blood flow rates in the cerebral vasculature can be estimated on a finer scale than prior methods. In various aspects small vessel segments can mean segments that are shorter than the lengths of most of the large arteries in the circle of Willis (e.g., internal carotids, middle cerebrals, vertebrals, etc), so that the blood flow rate through each vessel can be estimated.

By considering dispersion of the bolus, as a result of slower blood flow close to the arterial walls, the dispersion effect can be related to the underlying fluid mechanics. Previous methods of quantitative ASL MR angiography have either ignored dispersion, or modeled it with a statistical distribution of blood arrival times the parameters of which are difficult to interpret.

In addition, the ASL MRA techniques discussed in the present disclosure are not subject to the limitations of other angiographic techniques. In contrast to X-ray digital subtraction angiography (DSA), which is often used for cerebral angiography, ASL MRA techniques are less invasive for the patient and quicker to perform. In contrast to both X-Ray DSA and computed tomography angiography (CTA), ASL MRA techniques do not require exposing a patient to ionizing radiation or injecting a contrast agent into a patient, which carries the risk of an adverse or allergic reaction. Instead, ASL MRA techniques rely upon the magnetic properties of water molecules, such as those in a patient's blood, to provide endogenous contrast.

In the following discussion, a general description of various aspects of the present system, and its components, are provided, followed by a discussion of the methods and operation of the same. Several embodiments are presented as examples to illustrate the underlying principles of the present disclosure, including embodiments for pulsed ASL implementations and pseudo-continuous ASL implementations. However, other implementations involving other approaches are encompassed by the principles of present disclosure.

Figure 1:
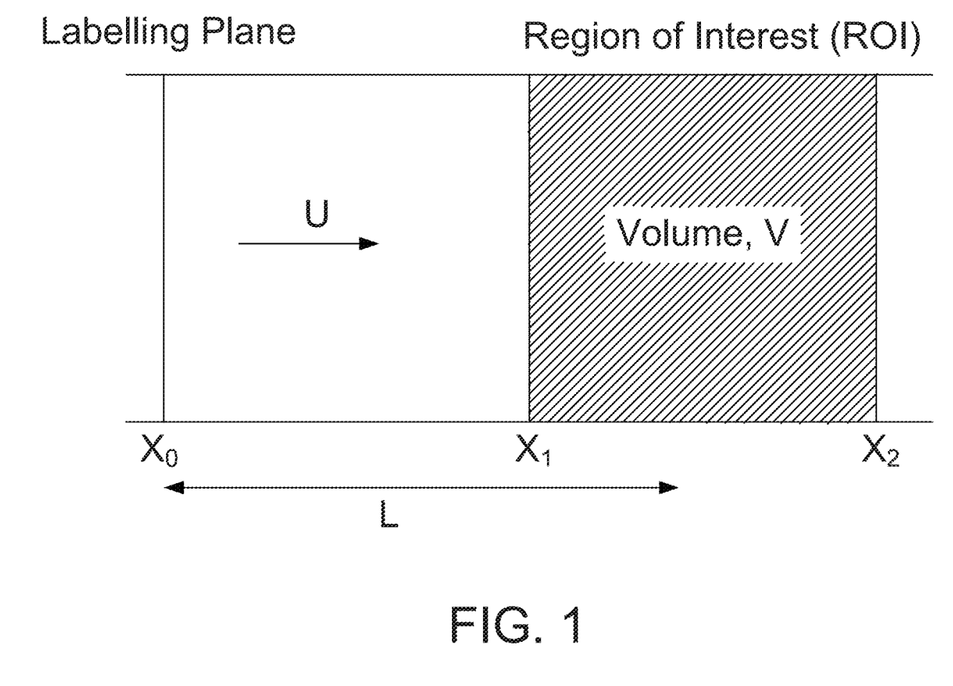
FIG. 1 is a schematic of a vessel modelled as a rigid-walled tube according to various embodiments of the present disclosure.

With reference to FIG. 1, depicted is a straight, axisymmetric cylinder with a detectable ASL tagged fluid (e.g. blood or other fluids) flowing through it. For pseudo-continuous ASL, a bolus of fluid passing through the cylinder will have a box-car shaped signal profile in the labelling plane. For pulsed ASL, the bolus of fluid passing through the cylinder can also have a box-car shaped signal profile in the labelling plane, just created differently than for pseudo-continuous ASL. The difference in the input functions for the two types of ASL (the input functions are given by equations 3 and 25) is the pulsed ASL input function can be a spatially defined box-car while the pseudo-continuous ASL input function can be a temporally defined box-car.

For embodiments implementing pulsed ASL, the concentration of the tag, represented by the variable c, is proportional to the pulsed ASL difference signal, which decays at a rate determined by $T_1$. This decay rate describes the longitudinal relaxation of the pulsed ASL signal. At any point along the vessel, c is given by the general mass transport equation:

$$\frac{\partial c(x,r,t)}{\partial t} + U(r)\frac{\partial c(x,r,t)}{\partial x} = -\frac{c(x,r,t)}{T_1} \quad (1)$$

where t is time, x is axial distance along the tube and $U(r)$ is the axial velocity profile of the fluid. Solutions to equation (1) take the form:

$$c(x,r,t) = f(x - U(r)t)e^{-t/T_1} \quad (2)$$

where $$f(x - U(r)t) = f(x_0) = c(x_0, r, 0)$$

The pulsed ASL signal created in the labelling plane is a rectangular pulse, which can be described mathematically as:

$$f(x) = H(x+\Delta) - H(x) \quad (3)$$

where $H(.)$ is the Heaviside unit step function and $\Delta$ is the spatial width of the pulsed ASL bolus created in the labelling plane. The input function $f(x)$ applies to the specific pulsed ASL imaging modality used in this example. However, different functions may be used here to model, for example, contrast agent injection, but the mathematical steps that follow to model the signal in an ROI would be the same.

Hence, $$f(x-U(r)t) = H(x-U(r)t+\Delta) - H(x-U(r)t) \quad (4)$$

The pulsed ASL difference signal measured at any point in the vessel is:

$$s(x,r,t) = S_0 c(x,r,t) = S_0 [H(x-U(r)t+\Delta) - H(x-U(r)t)]e^{-t/T_1} \quad (5)$$

where $S_0$ is a calibration factor that relates the measured pulsed ASL difference signal in a voxel to the volume of pulsed ASL tagged blood water present in the voxel. The pulsed ASL signal measured in a region of in an ROI is given by the integration of equation (5) over the volume V of the ROI, as provided below in equation (6).

$$S_{ROI}(t) = S_0 \int_{ROI} c(x,r,t) dV \quad (6)$$

RF excitation pulses attenuate the pulsed ASL signal of tagged water in the imaging region. The modified relaxation time t is shorter than $T_1$, meaning that the signal decays faster when in the imaging plane. To ensure a continuous signal after the initiation of imaging at $t=t_0$, when the modified relaxation time is used, the following scaling factor is applied:

$$S_{ROI}(t_0)e^{-t_0/T_1} = e^{-t_0(1/T_1 - 1/\tau)} S_{ROI}(t_0)e^{-t_0/\tau} \quad (7)$$

Meaning that $$S_{ROI}(t < t_0) = S_0 e^{-t/T_1} \int_{ROI} f(x - U(r)t) dV \quad (8)$$

$$S_{ROI}(t > t_0) = S_0 e^{-t/\tau} e^{-t_0(1/T_1 - 1/\tau)} \int_{ROI} f(x - U(r)t) dV \quad (9)$$

Hence, $$S_{ROI} = S_0 e^{-t/T_1} e^{-t_0(1/T_1 - 1/\tau)} \int_{ROI} [H(x - U(r)t + \Delta) - H(x - U(r)t)] dV \quad (10)$$

$$= S_0 e^{-t/T_1} e^{-t_0(1/T_1 - 1/\tau)} \int_{r=0}^{R} \int_{x_1}^{x_2} 2\pi r [H(x - U(r)t + \Delta) - H(x - U(r)t)] dr dx \quad (11)$$

$$= 2\pi R^2 S_0 e^{-t/T_1} e^{-t_0(1/T_1 - 1/\tau)} \int_{a=0}^{1} a \int_{x_1}^{x_2} [H(x - U(r)t + \Delta) - H(x - U(r)t)] dx da \quad (12)$$

where $a = r/R$.

From here onwards, the calibration factor and decay terms in equation 12 will be condensed into one time-dependent term, $g(t)$, as shown below:

$$S_{ROI} = 2\pi R^2 g(t) \int_{a=0}^{1} a[x - U(a)t + \Delta]H(x - U(a)t + \Delta) - (x - U(a)t)H(x - U(a)t)]_{x_1}^{x_2} da \quad (13)$$

$$= 2\pi R^2 g(t) \left\{ -\int_{a=0}^{1} (x_1 - U(a)t)H(U(a)t - x_1) a da + \int_{a=0}^{1} (x_2 - U(a)t)H(U(a)t - x_2) a da + \int_{a=0}^{1} (x_1 - U(a)t + \Delta)H(U(a)t - x_1 - \Delta) a da - \int_{a=0}^{1} (x_2 - U(a)t + \Delta)H(U(a)t - x_2 - \Delta) a da \right\} \quad (14)$$

Postulating a form for the velocity profile, $U(r)$ can be approximated by the following flow profile:

$$U(r) = \overline{U}\left(\frac{\gamma + 2}{\gamma}\right)\left(1 - \left(\frac{r}{R}\right)^\gamma\right) \quad (15)$$

Depending on the value of $\gamma$, $U(r)$ can take any form, from uniform plug flow to fully developed, parabolic, Hagen-Poiseuille flow. In equation 15, $\overline{U}$ is the average axial velocity of the fluid. The parameter $\gamma$ controls the shape of the velocity profile; it can take any value greater than 2 (parabolic flow) and as $\gamma \to \infty$ the velocity profile tends towards uniform plug flow. Hence, $\gamma$ controls the variation in the axial velocity with radius and can be seen as a measure of bolus dispersion.

The four integrals in equation (14) can all be solved using the same process, which is only demonstrated here for the first integral. Firstly, a Heaviside function is only equal to one when its argument is greater than zero, so:

$$H(U(a)t - x_1) = 1 \qquad (16)$$

when $$U(a)t > x_1$$

$$\overline{U}t\left(\frac{\gamma+2}{\gamma}\right)(1-a^\gamma) > x_1$$

$$(1-a^\gamma) > \frac{\gamma x_1}{(\gamma+2)\overline{U}t}$$

$$\left[1 - \frac{\gamma x_1}{(\gamma+2)\overline{U}t}\right]^{1/\gamma} > a$$

Including the flow profile model described by equation (15) in the first integral, termed $I_1$, and using equation (16) to redefine the limits of integration with respect to a gives:

$$I_1 = \int_{a=0}^{1}(x_1 - U(a)t)H(U(a)t - x_1)a\,da \qquad (17)$$

$$= \int_{a=0}^{[1-\frac{\gamma x_1}{(\gamma+2)\overline{U}t}]^{1/\gamma}}\left[ax_1 - \overline{U}t\left(\frac{\gamma+2}{\gamma}\right)(a-a^{\gamma+1})da\right]\cdot H(t-t_{min_1})$$

This exists when the upper limit of integration is larger than the lower limit:

$$0 < \left[1 - \frac{\gamma x_1}{(\gamma+2)\overline{U}t}\right]^{1/\gamma} \qquad (18)$$

Hence, $$t_{min_1} = \frac{\gamma x_1}{(\gamma+2)\overline{U}}$$

Integration and simplification of equation (17) gives:

$$I_1 = \frac{L}{2T}[t_{min_1} - t]\left[1 - \frac{t_{min_1}}{t}\right]^{2/\gamma}\cdot H(t-t_{min_1}) \qquad (19)$$

where $T = L/\overline{U}$. The three further integrals that made up equation (14) can all be solved in the same way as the first integral, leading to the following results:

$$I_2 = \frac{L}{2T}[t_{min_2} - t]\left[1 - \frac{t_{min_2}}{t}\right]^{2/\gamma}\cdot H(t-t_{min_2}) \quad \text{where } t_{min2} = \frac{\gamma x_2}{(\gamma+2)\overline{U}}$$

$$I_3 = \frac{L}{2T}[t_{min_3} - t]\left[1 - \frac{t_{min_3}}{t}\right]^{2/\gamma}\cdot H(t-t_{min_3}) \quad \text{where } t_{min3} = \frac{\gamma(x_1+\Delta)}{(\gamma+2)\overline{U}}$$

$$I_4 = \frac{L}{2T}[t_{min_4} - t]\left[1 - \frac{t_{min_4}}{t}\right]^{2/\gamma}\cdot H(t-t_{min_4}) \quad \text{where } t_{min4} = \frac{\gamma(x_2+\Delta)}{(\gamma+2)\overline{U}}$$

The final model of the measured pulsed ASL signal, integrated over an ROI, is:

$$S_{ROI} = BFg(t)\Big\{-[t_{min_1} - t]\left[1 - \frac{t_{min_1}}{t}\right]^{2/\gamma}\cdot H(t-t_{min_1}) + \qquad (20)$$

$$[t_{min_2} - t]\left[1 - \frac{t_{min_2}}{t}\right]^{2/\gamma}\cdot H(t-t_{min_2}) +$$

$$[t_{min_3} - t]\left[1 - \frac{t_{min_3}}{t}\right]^{2/\gamma}\cdot H(t-t_{min_3}) -$$

$$[t_{min_4} - t]\left[1 - \frac{t_{min_4}}{t}\right]^{2/\gamma}\cdot H(t-t_{min_4})\Big\}$$

where $$BF = \frac{\pi R^2 L}{T} = \pi R^2 \overline{U} \qquad (21)$$

For pseudo-continuous ASL embodiments, propagation of the ASL 'labeled' fluid (e.g. blood) is governed by the mass transport equation:

$$\frac{\partial c(x,r,t)}{\partial t} + U(r)\frac{\partial c(x,r,t)}{\partial x} = -\frac{c(x,r,t)}{T_{1b}} \qquad (22)$$

where $c(x,r,t)$ is the proportion of fluid that is ASL labelled, $T_{1b}$ is the longitudinal relaxation time of arterial blood, x is the distance from the labelling plane, t is time from initiation of labelling and $U(r)$ is the axial velocity profile of blood, given by:

$$U(r) = \overline{U}\left(\frac{\gamma+2}{\gamma}\right)\left(1 - \left(\frac{r}{R}\right)^\gamma\right) \qquad (23)$$

where r is radial position, R is the internal radius of the artery, and $\overline{U}$ is the average axial flow velocity. The $\gamma$ parameter controls the shape of the bolus, accounting for its dispersion due to slower flow near the vessel wall. The parameter can take any value in the range $2 \leq \gamma < \infty$, the extremes of which give Pouiseuille (laminar) and plug flow, respectively.

Taking the Laplace transform of equation (22), with the initial condition, $c(x,r,0)=0$, gives the following Laplace-domain solution:

$$c(x,r,s) = Be^{-sx/U(r)}e^{-x/U(r)T_{1b}} \qquad (24)$$

where B is the constant of integration and s is frequency in the Laplace-domain. In contrast to pulsed ASL, pseudo-continuous ASL involves labelling the different parts of the bolus of labelled blood at different time points. As a result, equations for modelling pulsed ASL embodiments can be inaccurate when modelling the decay of the pseudo-continuous ASL label because signals corresponding to different parts of the bolus will have spent different amounts of time decaying. Therefore, as shown in equation 24, pseudo-continuous ASL accounts for the difference in decay by accounting for the decay spatially. If the leading and trailing edge of the bolus move with the same axial velocity profile $U(r)$, then one can determine how long a part of the bolus has existed, and therefore how long the part of the bolus has been decaying, by how far it has travelled.

Equation 25 defines the boundary condition for pseudo-continuous ASL at 40, the labelling plane:

$$c(x_0,t) = H(t) - H(t-\tau) \qquad (25)$$

Where $H(.)$ is the unit step function and $\tau$ is the pseudo-continuous ASL labelling duration. The bolus duration can be defined temporally in pseudo-continuous ASL embodiments because the width of bolus is determined by how long a narrow plane in the neck is labelled. In contrast, pulsed ASL embodiments can use a wide labelling as the width of the bolus is defined by the width of the labelling plane. Accordingly, in the Laplace domain, equation (25) can be used to eliminate B, in equation 24. Hence, the exact time-domain solution to equation 22 is:

$$c(x, r, t) = \left[H\left(t - \frac{x}{U(r)}\right) - H\left(t - \frac{x}{U(r)} - \tau\right)\right] e^{-x/U(r)T_{1b}} \quad (26)$$

However, the signal from the pseudo-continuous ASL label is attenuated by the RF excitation pulses it experiences as it passes through the imaging region. this effect is accounted for by multiplying equation 26 by a term which effectively hastens the longitudinal relaxation of the pseudo-continuous ASL label:

$$c(x,r,t<t_0)=c(x,r,t) \quad (27)$$

$$c(x,r,t>t_0)=e^{(t-t_0)\ln(\cos\alpha)/T_R}c(x,r,t) \quad (28)$$

where $t_0$ is the time at which imaging begins, $\alpha$ is the flip angle of the RF excitation pulses, and $T_R$ is their repetition time.

The MR signal, at any point in an artery, is related to the amount of pseudo-continuously ASL labelled blood, by the calibration factor, $S_0$:

$$s(x,r,t)=S_0 c(x,r,t) \quad (29)$$

In order to estimate the volume flow rate of blood through an artery, equation 29 can be integrated over the volume of a region of interest in order to model the passage of the bolus into, and through, a vessel segment in the region of interest, as illustrated in equation 30 and 31:

$$S_{ROI}(t > t_0) = S_0 e^{(t-t_0)\ln(\cos\alpha)/T_R} \int_{r=0}^{R} \int_{x_1}^{x_2} 2\pi r \left[H\left(t - \frac{x}{U(r)}\right) - H\left(t - \frac{x}{U(r)} - \tau\right)\right] e^{-x/U(r)T_{1b}} dx dr \quad (30)$$

$$= S_0 \pi R^2 \int_{\alpha=0}^{1} \alpha \int_{x_1}^{x_2} 2 \left[H\left(t - \frac{x}{U(r)}\right) - H\left(t - \frac{x}{U(r)} - \tau\right)\right] e^{-x/U(r)T_{1b}} dx d\alpha \quad (31)$$

where $\alpha=r/R$. During the integration by parts of equation 31, the constants: $\bar{U}$, $(\gamma+2)/\gamma$, and $T_{1b}$ are taken outside of both of the integrals. In the case of no bolus dispersion, i.e. plug flow ($\gamma \to \infty$ in equation 23), the radial integral in equation 31 is tractable and the solution is:

$$S_{ROI}(t > t_0) = \quad (32)$$
$$FS_0 T_{ib} e^{(t-t_0)\ln(\cos\alpha)/T_R} \{[e^{-x_1/U(\tau)T_{1b}} - e^{-t/T_{1b}}] \cdot H(t-t_1) - [e^{-x_2/U(\tau)T_{1b}} - e^{-t/T_{1b}}] \cdot H(t-t_2) - [e^{-x_1/U(\tau)T_{1b}} - e^{(\tau-t)/T_{1b}}] \cdot H(t-t_3) + [e^{-x_2/U(\tau)T_{1b}} - e^{(\tau-t)/T_{1b}}] \cdot H(t-t_4)\}$$

where F is the net flow rate of blood through the arterial segment. In equation 32, $F=\pi R^2 \bar{U}$, $t_1=x_1/\bar{U}$, $t_2=x_2/\bar{U}$, $t_3=t_1+T$, and $t_4=t_2+T$.

However, in the case of dispersion, the radial integral in equation 31 is not tractable and should be solved numerically. Like equation 32, the solution is an equation made up of four groups of terms, each of which contributes to the signal only after a certain time point has been reached. For example, $t_1$ refers to the time at which the leading edge of the pseudo-continuously ASL labeled blood bolus arrives in the region of interest. The four time parameters are explained in FIG. 2B below.

Figure 2A:
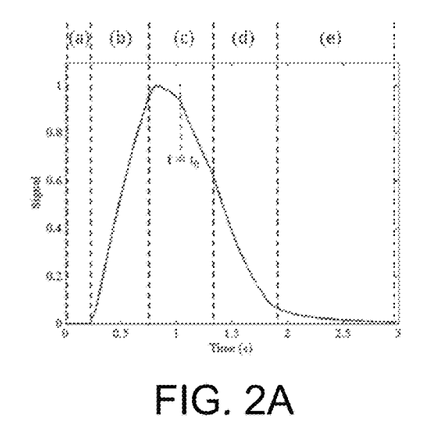
FIGS. 2A and 2B depict examples of ASL MRI signal modeled in a region of interest (ROI), according to various embodiments of the present disclosure.
Figure 2B:
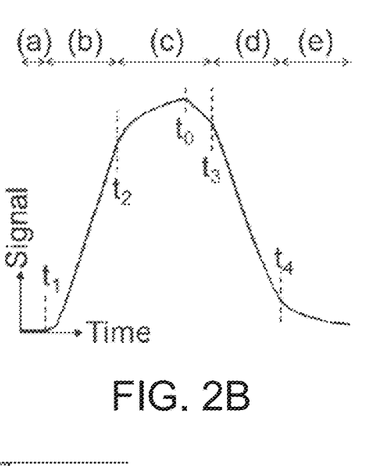
Figure 2C:
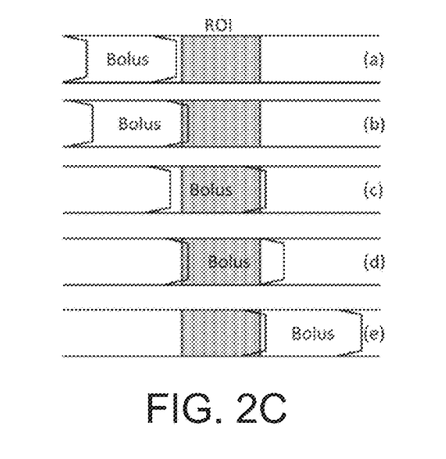
FIG. 2C depicts five exemplary distinct states of the passage of the bolus of blood through the vessel.

FIGS. 2A-2C depict an example of the ASL MRI signal modelled pulsed ASL and pseudo-continuous ASL approaches. FIG. 2A depicts a time plot for pulsed ASL approaches. FIG. 2B depicts a time plot for pseudo-continuous approaches. FIG. 2C depicts the status of a bolus of blood as it passes through a region of interest (ROI) being modeled with pulsed ASL or pseudo-continuous ASL approaches.

In FIG. 2A the dotted line at $t=t_0$ signals the beginning of imaging for pulsed ASL approaches. At this time point, the bolus starts to undergo the attenuating effects of the RF imaging pulses, hence the change in the signal gradient. In FIG. 2B, $t=t_0$ signals the beginning of imaging for pseudo-continuous ASL approaches.

In FIG. 2C, five (5) distinct states are depicted corresponding to the states plotted in FIG. 2A or FIG. 2B. Although the distinct states are similar in nature, they are modelled slightly differently using pulsed ASL approaches in comparison with pseudo-continuous ASL approaches.

For pulsed ASL approaches, the five distinct states depicted in FIG. 2C corresponding to the time plot in FIG. 2A are:
  (a) $t<t_1$—There is no pulsed ASL tagged blood in the ROI and, therefore, no signal.
  (b) $t_1<t<t_2$—The leading edge of the bolus has arrived in the ROI. The volume of pulsed ASL tagged blood in the ROI rapidly increases, as does the signal amplitude.
  (c) $t_2<t<t_3$—The leading edge of the bolus begins to leave the ROI. At this point the volume of pulsed ASL tagged blood in the ROI remains constant as blood flows into and out of the region at the same flow rate. Even so, the measured signal amplitude declines, initially influenced by the longitudinal relaxation of $T_1$. When imaging commences at $t=t_0$, the decline occurs more rapidly, influenced by the shorter, modified relaxation time $\tau$.
  (d) $t_3<t<t_4$—The trailing edge of the bolus arrives in the ROI, meaning the pulsed ASL signal amplitude decreases rapidly because more tagged blood leaves the ROI than enters it.
  (e) $t_4<t$—As the trailing edge of the bolus leaves the ROI, the pulsed ASL signal gradually tails away.

The pulsed ASL signal measured in each voxel of an image can be thought of as the integral of s(x, r, t) over the volume of the voxel, hence, the measured signal in an ROI was calculated from an image by summing the pulsed ASL signals from every voxel in the ROI. The parameters of the flow model were estimated by finding the set of parameter values which minimized the RMS error between measured and modelled pulsed ASL signals in an ROI.

In this particular example the fact that imaging did not commence until tagging was complete meant that most of the vessels in the angiograms were already filled with pulsed ASL tagged blood at t=t0=1.028 s. As a result, most of the measured signals contained no information about the inflow of tagged blood into the ROI. So, only the part of the model which included the effects of imaging, i.e. from 1.028 s onwards, was thus used. However, we may start imaging before or after the bolus arrives, depending on how long the tag duration is and how long it takes the blood to arrive.

In order to obtain more information about the bolus' passage, the pulsed ASL signals from two regions (an 'input' region and a downstream ROI) were used. Estimation of the timing parameters was expected to be easier using the signal from the downstream ROI, because the signal would be delayed relative to the signal from the input region. Hence, it would provide more information about the accumulation of the tag in the region. The modelled signals for the input region and the downstream ROI were fitted to the corresponding measured signals. The blood flow rate, BF, and the dispersion parameter, γ, were assumed to be common to the blood flow between the two regions. This can reduce the number of model parameters used to define the two models to: BF, γ, $t1_{ROI}$, $t2_{ROI}$, $t3_{ROI}$, $t4_{ROI}$, $t1_{in}$, $t2_{in}$, $t3_{in}$, and $t4_{in}$ (ten parameters in total).

Estimation of the ten model parameters from just forty data points (twenty time points for each region's signal) was a poorly conditioned problem. To limit the number of parameters that were estimated from model fitting, the following three assumptions can be made:

1. The temporal width of the bolus does not change, i.e. no further dispersion of the bolus occurred, as it passed through a region:

$$t_3 - t_1 = t_4 - t_2 \quad (33)$$

Hence $$t1_{ROI} = t2_{ROI} + t3_{ROI} - t4_{ROI} \quad (34)$$

$$t1_{in} = t2_{in} + t3_{in} - t4_{in} \quad (35)$$

2. The temporal width of the bolus does not change, i.e. no further dispersion occurs, between the input region and the downstream ROI:

$$t4_{in} - t2_{in} = t4_{ROI} - t2_{ROI}$$

$$t2_{in} = t4_{in} + t2_{ROI} - t4_{ROI} \quad (36)$$

Figure 3A:
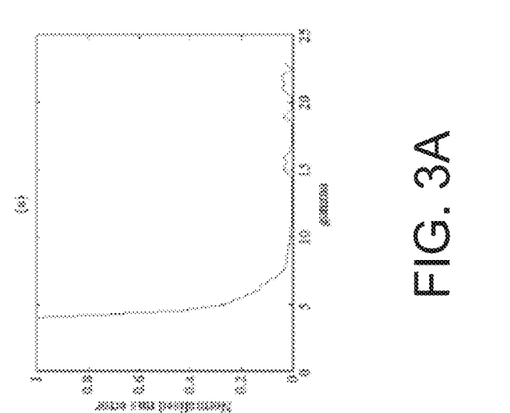
FIGS. 3A-3C are drawings of typical values of RMS error between the estimated and known flow rates in a flow phantom, according to various embodiments of the present disclosure. The figures show errors in flow rates using an input region in: A) small, B) medium, and C) large downstream ROI.
Figure 3B:
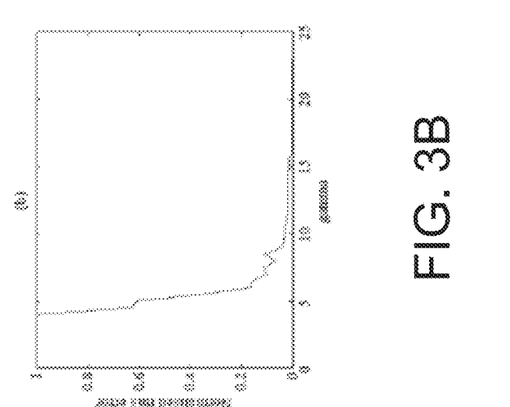
Figure 3C:
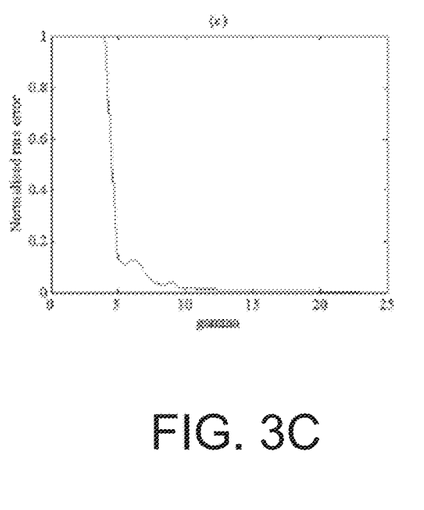

3. The dispersion parameter takes a fixed value. During preliminary experiments it was found that estimating the dispersion parameter, γ, is particularly difficult. In initial investigations, model fitting was performed, and repeated with γ fixed at a different value each time. The RMS error, between the eight estimated water flow rates and the eight known flow rates, was used to find the most suitable value of γ. The results of these initial experiments for three different downstream ROI sizes are shown in FIGS. 3A-3C. The value γ=12 was chosen as it gave a consistently low RMS error for all of the regions considered.

After making these three assumptions, the parameters to be estimated during curve fitting were BF, $t2_{ROI}$, $t3_{ROI}$, $t4_{ROI}$, $t3_{in}$, and $t4_{in}$.

The modelled pulsed ASL signals may be fitted to the measured signals using the Nelder-Mead simplex algorithm, which is a direct search method for minimizing a scalar-valued non-linear function, or similar approaches. The modelled pulsed ASL signal function, as illustrated by equation (20), is discontinuous with the timing parameters $t_2$, $t_3$, and $t_4$. Direct search methods, such as the Nelder-Mead simplex algorithm, which use only cost function evaluations, not derivatives, may be able to handle these discontinuities in a robust manner. Furthermore, direct search methods, such as the Nelder-Mead simplex algorithm, can sometimes be very efficient in finding minimizers.

However, the Nelder-Mead algorithm may be sensitive to initial conditions. Hence, the model parameters can be initialized as follows:

1. Blood flow rate—For pulsed ASL signals from ROIs in images of the flow phantom, the blood flow rate parameter can be initialized at the known flow rate. For example, for ROIs in images of the circle of Willis, mean values from literature may be used.
2. Time parameters—$t2_{ROI}$, $t3_{ROI}$, $t4_{ROI}$, $t3_{in}$, and $t4_{in}$ can be initialized by visual identification of the limits of flow stages (c) and (d) in FIG. 2 in each of the measured pulsed ASL region signals. They also can be estimated from simple metrics like the time at which the signal drops to half its maximum value.

For pseudo-continuous ASL approaches, the five distinct states depicted in FIG. 2C, corresponding FIG. 2B shows the pseudo-continuously modelled ASL MR signal evolution. The four time parameters depicted in FIG. 2B are given by the following equations:

$$t_1 = \frac{\gamma x_1}{(\gamma + 2)\overline{U}} \quad (37)$$

$$t_2 = \frac{\gamma x_2}{(\gamma + 2)\overline{U}} \quad (38)$$

$$t_3 = t_1 + \tau \quad (39)$$

$$t_4 = t_2 + \tau \quad (40)$$

The signal is initially detected at stage (b) (FIG. 2C), after the arrival of the leading edge of the bolus at $t_1$. It then levels out in stage (c) (FIG. 2C) after the leading edge of the bolus begins to leave the region of interest, reducing the rate of accumulation of tagged blood. Coupled with the attenuating effects of RF pulses, which begin at $t_0$, this leads to a decrease in the signal intensity. The signal decreases as the bolus's trailing edge arrives—stage (d) (FIG. 2C)—and then leaves the vessel segment—stage (e) (FIG. 2C).

Figure 4:
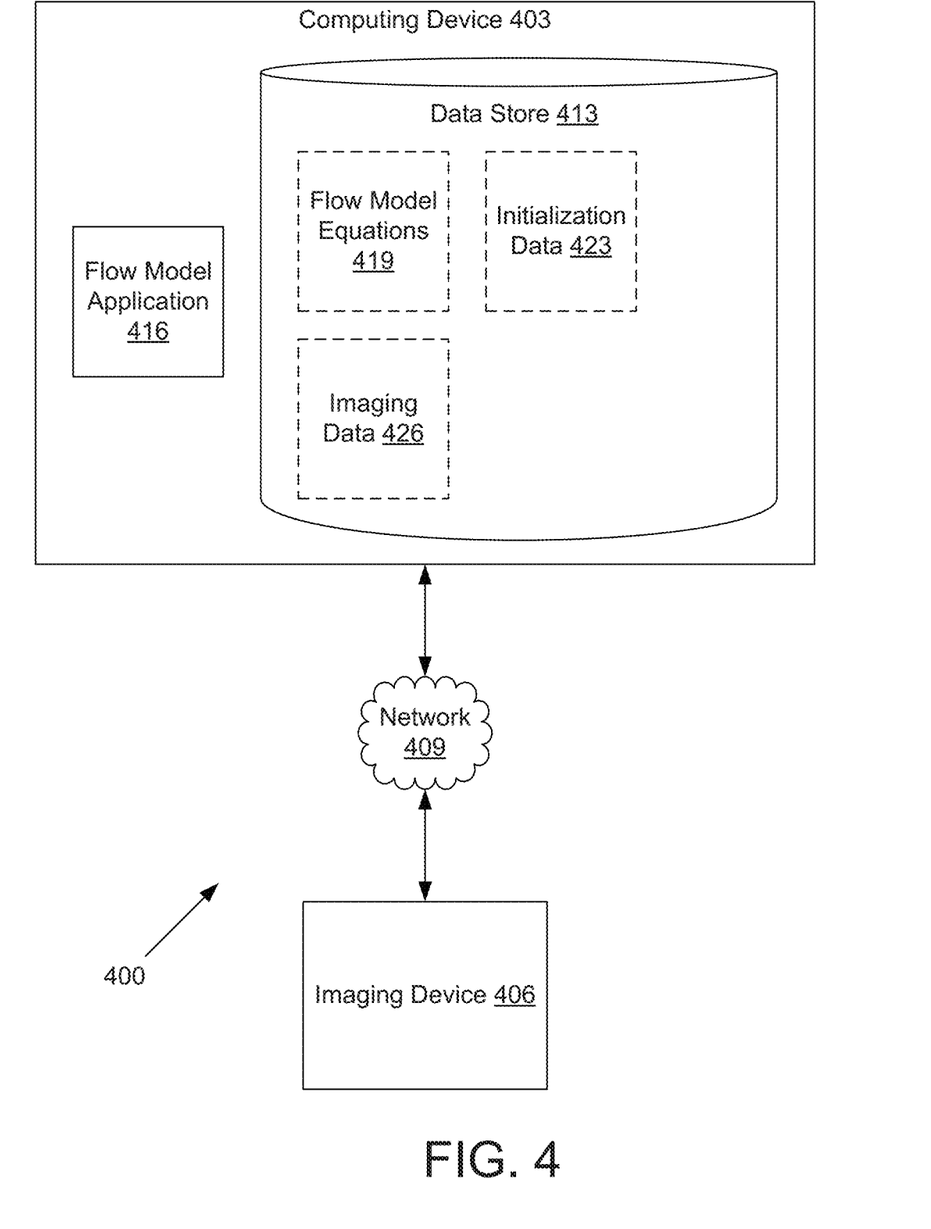
FIG. 4 is a schematic block diagram that provides one example illustration of a networked environment according to various embodiments of the present disclosure.

With reference to FIG. 4, shown is a networked environment 400 according to various embodiments. The networked environment 400 includes a computing device 403, an imaging device 406, and potentially other devices, which are in data communication with each other via a network 409. The network 409 includes, for example, the Internet, intranets, extranets, wide area networks (WANs), local area networks (LANs), wired networks, wireless networks, or other suitable networks, etc., or any combination of two or more such networks. For example, such networks may comprise satellite networks, cable networks, Ethernet networks, and other types of networks.

The computing device 403 can include, for example, a server computer or any other system providing computing capability. Alternatively, the computing device 403 may correspond to a plurality of computing devices 403 that may be arranged, for example, in one or more server banks or computer banks or other arrangements. Such computing devices 403 may be located in a single installation or may be distributed among many different geographical locations. For example, the computing device 403 may correspond to a plurality of computing devices 403 that together may comprise a hosted computing resource, a grid computing resource and/or any other distributed computing arrangement. In some cases, the computing device 403 may correspond to a virtualized computing device 403, such as an elastic computing resource where the allotted capacity of processing, network, storage, or other computing-related resources may vary over time.

Various applications and/or other functionality may be executed in the computing device 403 according to various embodiments. Also, various data is stored in a data store 413 that is accessible to computing device 403. The data store 413 may be representative of a plurality of data stores 413 as can be appreciated. The data stored in the data store 413, for example, is associated with the operation of the various applications and/or functional entities described below.

The components executed on the computing device 403, for example, include a flow model application 416, and other applications, services, processes, systems, engines, or functionality not discussed in detail herein. The flow model application 416 is executed to model the flow of blood in a specified region of interest (ROI) in the manner previously described. The flow model application 416 may accomplish this, for example, by estimating how long a bolus of a contrast agent, such as a contrast agent used in arterial spin labeling, takes to traverse a particular region of interest.

The data stored in the data store 413 includes, for example, the flow model equations 419, initialization data 423, imaging data 426 and potentially other data. The flow model equations 419 correspond to the previously described equations (1) through (25) for use in modeling the flow of blood through a region of interest. The initialization data 423 corresponds to the data necessary to initialize the equations used to model the flow of blood through a region of interest. The initialization data 423 may include, for example, average blood flow rates through various anatomical structures and/or portions of the circulatory system. The initialization data 423 may also include various timing data, as previously described. The imaging data 426 represents data generated by the imaging device 406, from which the flow model application 416 may estimate blood flow parameters using the flow model equations 419.

The imaging device 406 is representative of any one of a number of imaging devices 406 coupled to the network 409. The imaging device 406 may correspond to, for example, a magnetic imaging device 406, an x-ray imaging device, a positron emission topography (PET) imaging device 406, and/or other types of imaging devices 406 suitable for generating the necessary data for processing by the flow model application 416. The imaging device 406 may be configured to send and/or store imaging data 426 in a data store 413. In some embodiments, the imaging device 406 may be configured to execute an appropriate client application to perform this functionality.

Next, a general description of the operation of the various components of the networked environment 400 is provided. To begin, a patient is imaged using the imaging device 406. Data is generated by the imaging device 406 at regular time intervals. The data generated may correspond to data for a particular region of interest of a patient, such as a particular anatomical structure, and the data may include blood flow data at each time interval. The imaging device 406 may then store the data as imaging data 426.

After the imaging data 426 has been generated and stored by the imaging device 406, the flow model application 416 uses initialization data 423 to initialize the flow model represented by the flow model equations 419. The flow model application 416 then models the flow of blood through the imaged region of interest by solving the flow model equations 419 using the imaging data 426.

Figure 5:
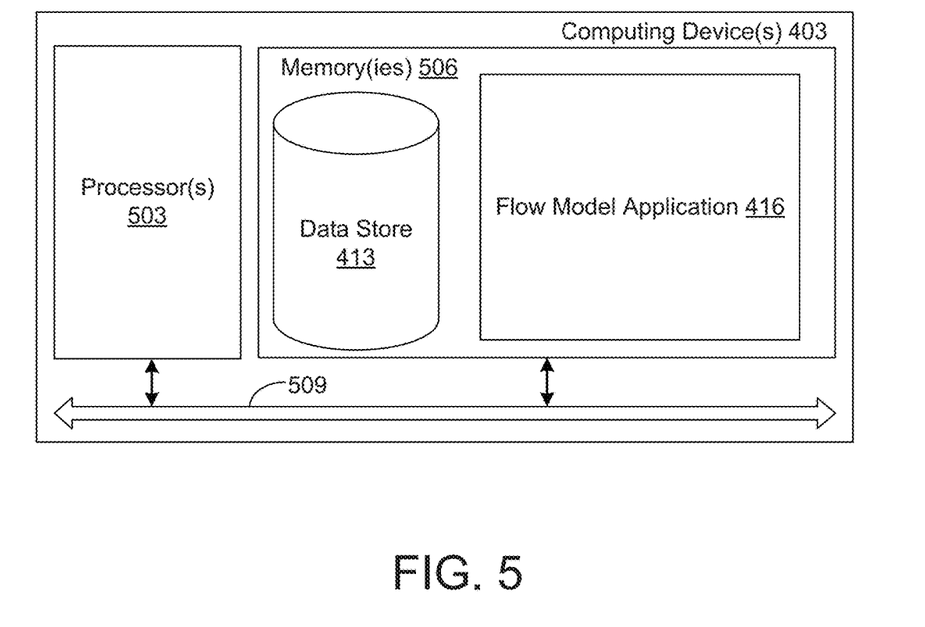
FIG. 5 is a schematic block diagram that provides one example illustration of a computing device employed in the networked environment of FIG. 4 according to various embodiments of the present disclosure.

With reference to FIG. 5, shown is a schematic block diagram of a computing device 403, according to various embodiments of the present disclosure. The computing device 403 includes at least one processor circuit, for example, having a processor 503 and a memory 506, both of which are coupled to a local interface 509. The local interface 509 may comprise, for example, a data bus with an accompanying address/control bus or other bus structure as can be appreciated.

Stored in the memory 506 are both data and several components that are executable by the processor 503. In particular, stored in the memory 506 and executable by the processor 503 are flow model application 416 and potentially other applications. Also stored in the memory 506 may be a data store 413 and other data. In addition, an operating system may be stored in the memory 506 and executable by the processor 503.

It is understood that there may be other applications that are stored in the memory 506 and are executable by the processor 503 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Flash®, or other programming languages.

A number of software components are stored in the memory 506 and are executable by the processor 503. In this respect, the term "executable" means a program file that is in a form that can ultimately be run by the processor 503. Examples of executable programs may be, for example, a compiled program that can be translated into machine code in a format that can be loaded into a random access portion of the memory 506 and run by the processor 503, source code that may be expressed in proper format such as object code that is capable of being loaded into a random access portion of the memory 506 and executed by the processor 503, or source code that may be interpreted by another executable program to generate instructions in a random access portion of the memory 506 to be executed by the processor 503, etc. An executable program may be stored in any portion or component of the memory 506 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 506 is defined herein as including both volatile and nonvolatile memory and data storage components. Volatile components are those that do not retain data values upon loss of power. Nonvolatile components are those that retain data upon a loss of power. Thus, the memory 506 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 503 may represent multiple processors 503 and/or multiple processor cores and the memory 506 may represent multiple memories 506 that operate in parallel processing circuits, respectively. In such a case, the local interface 509 may be an appropriate network that facilitates communication between any two of the multiple processors 503, between any processor 503 and any of the memories 506, or between any two of the memories 506, etc. The local interface 509 may comprise additional systems designed to coordinate this communication, including, for example, performing load balancing. The processor 503 may be of electrical or of some other available construction.

Although the flow model application 416, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The program instructions for embodiments of the flow model application 416 may be embodied in the form of source code that comprises human-readable statements written in a programming language or machine code that comprises numerical instructions recognizable by a suitable execution system such as a processor 503 in a computer system or other system. The machine code may be converted from the source code, etc. If embodied in hardware, each block may represent a circuit or a number of interconnected circuits to implement the specified logical function(s).

Although a specific order of execution is discussed, it is understood that the order of execution may differ from that which is depicted. For example, the order of execution of two or more portions of the flow model application 416 may be scrambled relative to the order described. Also, two or more portions of the flow model application 416 may be executed concurrently or with partial concurrence. Further, in some embodiments, portions of the flow model application 416 that have been previously described may be skipped and/or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including flow model application 416, that comprises software or code can be embodied in any non-transitory computer-readable medium for use by or in connection with an instruction execution system such as, for example, a processor 503 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

The computing device 403 shown in FIG. 5 or the imaging device 406 of FIG. 4, or both, may be embodied, for example, as a magnetic resonance apparatus, that may include a processing module or logic for performing conditional data processing, and may be implemented either off-line or directly in a magnetic resonance apparatus. For such embodiments, computing device 403 or imaging device 406 or both may be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present devices, systems and methods may be implemented are described in U.S. Pat. Nos. 5,993,398 and 6,245,027 and U.S. Publication No. 2011/0181285, which are incorporated by reference as if fully set forth herein.

Further, any logic or application described herein, including flow model application 416, may be implemented and structured in a variety of ways. For example, one or more applications described may be implemented as modules or components of a single application. Further, one or more applications described herein may be executed in shared or separate computing devices or a combination thereof. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should further be noted that the disclosure is not limited to the embodiments previously described, but may also include additional functionality or more correspond to additional embodiments.

Therefore, the following is claimed:

1. A system, comprising:

at least one computing device;

an imaging device in data communication with the at least one computing device, the imaging device configured to acquire an image of a region of interest of a blood vessel; and an application executed in the at least one computing device, the application comprising non-transitory computer-readable media comprising machine readable instructions that, when executed, cause the at least one computing device to at least:

identify a passage of a bolus of fluid through the region of interest of the imaged blood vessel over a period of time; and estimate, with a mass transit model, blood flow through the region of interest of the imaged blood vessel based at least in part on the passage of the bolus of fluid through region of interest of the imaged blood vessel during the period of time.

2. The system of claim 1, wherein causing the at least one computing device to estimate the blood flow through the imaged blood vessel further comprises causing the at least one computing device to at least estimate the blood flow based at least in part on an anatomical data of the blood vessel.

3. The system of claim 1, wherein the bolus of fluid comprises an arterial spin labeling (ASL) tagged bolus of fluid.

4. The system of claim 3, wherein the ASL tagged bolus of fluid corresponds to a pulsed ASL tagged bolus of fluid.

5. The system of claim 3, wherein the ASL tagged bolus of fluid corresponds to a pseudo-continuous ASL tagged bolus of fluid.

6. The system of claim 3, wherein the arterial spin labeling (ASL) tagged bolus of fluid has a box-car signal profile.

7. The system of claim 1, wherein the mass transit model includes an axial velocity profile of the bolus of fluid.

8. The system of claim 1, wherein causing the at least one computing device to at least estimate, with a mass transit model, blood flow through the region of interest of the imaged blood vessel estimates variation in axial velocity with radius of the bolus of fluid passing through the region of interest of the imaged blood vessel.

9. The system of claim 1, wherein the application causes the at least one computing device to at least acquire dynamic angiographic data which covers the region of interest of the imaged blood vessel in a subject.

10. The system of claim 9, wherein causing the at least one computing device to acquire the dynamic angiographic data comprises causing the at least one computing device to acquire the angiographic data from a medical imaging device, and wherein the subject is positioned in association with the medical imaging device and the medical imaging device is used to acquire the dynamic angiographic data.

11. A method, comprising:

tracking, via a computing device, a passage of a bolus of fluid through an imaged blood vessel over a period of time;

fitting, via the computing device, the tracked passage of the bolus of fluid to a modeled passage of the bolus of fluid, wherein the modeled passage of the bolus of fluid is based at least in part on a mass transit model; and estimating, via the computing device, a volume of blood flow through the imaged blood vessel based at least in part on a fit of the tracked passage of the bolus of fluid to the modeled passage of the bolus of fluid.

12. The method of claim 11, further comprising initializing, via the computing device, the modeled passage of the bolus of fluid based at least in part on anatomical data of the imaged blood vessel.

13. The method of claim 11, wherein fitting the tracked passage of the bolus of fluid to the modeled passage of the bolus of fluid is based at least in part upon a direct search method.

14. The method of claim 13, wherein the direct search method comprises a Nelder-Mead simplex approach.

15. The method of claim 11, wherein the bolus of fluid comprises a pulsed arterial spin labeling (ASL) tagged bolus of fluid.

16. The method of claim 11, wherein the bolus of fluid comprises a pseudo-continuous arterial spin labeling (ASL) tagged bolus of fluid.

17. The method of claim 11, wherein the mass transit model includes an axial velocity profile of the bolus of fluid.

18. The method of claim 11, wherein the mass transit model estimates variation in axial velocity with radius of the bolus of fluid passing through the region of interest of the imaged blood vessel.

19. The method of claim 11, comprising acquiring dynamic angiographic data which covers the region of interest of the imaged blood vessel in a subject.

20. The method of claim 19, wherein acquiring the dynamic angiographic data comprises acquiring the angiographic data from a medical imaging device, positioning the subject in association with the medical imaging device, and using the medical imaging device to acquire the dynamic angiographic data.

* * * * *